US00PP26545P3

(12) United States Plant Patent
Tristram

(10) Patent No.: US PP26,545 P3
(45) Date of Patent: Mar. 29, 2016

(54) ***RHODODENDRON* PLANT NAMED 'WALSANBARB'**

(50) Latin Name: ***Rhododendron kaempferi* hybrid**
Varietal Denomination: WALSANBARB

(71) Applicant: David Tristram, Arundel (GB)

(72) Inventor: David Tristram, Arundel (GB)

( * ) Notice: Subject to any disclaimer, the term of this patent is extended or adjusted under 35 U.S.C. 154(b) by 112 days.

(21) Appl. No.: 14/120,709

(22) Filed: Jun. 17, 2014

(65) Prior Publication Data

US 2014/0380536 P1 Dec. 25, 2014

Related U.S. Application Data

(60) Provisional application No. 61/956,955, filed on Jun. 20, 2013.

(51) Int. Cl.
*A01H 5/00* (2006.01)
*A01H 5/02* (2006.01)

(52) U.S. Cl.
USPC ..... Plt./239
CPC ..... *A01H 5/02* (2013.01)

(58) Field of Classification Search
USPC ..... Plt./239
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new and distinct variety of *Rhododendron* plant named 'WALSANBARB' which is characterized by compact mounding habit, glossy evergreen foliage, large single flowers in a light shell-pink color with light speckling which are produced from late spring through early summer, is disclosed.

2 Drawing Sheets

Genus and species: *Rhododendron kaempferi* hybrid.
Variety denomination: 'WALSANBARB'.

CROSS-REFERENCE TO RELATED APPLICATIONS

This application claims the benefit of priority under 35 U.S.C. 119 of U.S. Provisional application Ser. No. 61/956,955 filed on Jun. 20, 2013 entitled "*Rhododendron* Plant Named 'WALAZ41'" and for which the inventor now wishes to file this application with the cultivar name or denomination 'WALSANBARB'.

BACKGROUND OF THE NEW PLANT

The present invention relates to a new and distinct cultivar of *Rhododendron*, also commonly known as evergreen azalea, which is grown as an ornamental shrub for use in planted containers and in the garden and landscape. The new cultivar is known botanically as *Rhododendron kaempferi* hybrid, and will be referred to hereinafter by the cultivar name 'WALSANBARB'.

'WALSANBARB' arose and was selected from a long term breeding program commenced by the inventor in 1993 or 1994. The aim of the breeding program was to develop one or more matched series of novel cultivars of hardy evergreen azaleas with showy flowers. Another objective of the breeding program was to develop large open-faced single flowers and also heavily flowering double flower forms. Breeding commenced with Azalea 'Elsie Lee' as one of the initial parents. Azalea 'Elsie Lee' is a Shammarello hybrid, raised in Ohio in the 1960s and renowned for its relative hardiness among evergreen azaleas. Although several Shammarello hybrids were patented in the 1960s and 1970s, the inventor believes that Azalea 'Elsie Lee' was unpatented. 'Elise Lee' bears light mauve-blue semi-double flowers.

Commencing in 1993 or 1994, the many generations of deliberate hybrids were raised, selecting promising parents from his collection of previous unnamed seedlings which had been raised during the breeding program. 'WALSANBARB' was selected in 2003 or 2004. The parents of 'WALSANBARB' are unknown to the inventor and have not been retained. Thus, no parental comparison information is available.

Asexual propagation of 'WALSANBARB' was first accomplished in 2003 or 2004 using semi-ripe shoot cuttings. Since that time, under careful observation, the distinguishing characteristics of 'WALSANBARB' have been determined stable and uniform, and to reproduce true to type in successive generations of asexual propagation via semi-ripe shoot cuttings.

SUMMARY OF THE NEW VARIETY

The distinguishing characteristics of 'WALSANBARB' are listed below. 'WALSANBARB' has not been tested under all possible conditions and phenotypic differences may be observed with variations in environmental, climatic, and cultural conditions.

1. Plants of 'WALSANBARB' exhibit a compact mounding growth habit.
2. The foliage of 'WALSANBARB' is glossy evergreen in color.
3. 'WALSANBARB' bears large, 9.0 cm diameter, single flowers in a light shell-pink color with light speckling.
4. Plants of 'WALSANBARB' show good heat and humidity tolerance.
5. 'WALSANBARB' blooms from late spring through early summer.
6. After two years of growth, plants of 'WALSANBARB' are 20 cm to 25 cm in height and 25 cm to 30 cm in width.

7. At maturity, 5 years, plants of 'WALSANBARB' are 30 cm to 40 cm in height and 35 cm to 45 cm in width.
8. 'WALSANBARB' prefers semi-shade in a moist, well drained, slightly acidic growing media.
9. 'WALSANBARB' is suitable for use as a garden specimen, landscape plants and as a container specimen.
10. 'WALSANBARB' is hardy to at least USDA Zone 7.

DESCRIPTION OF THE PHOTOGRAPHS

The accompanying color photographs illustrate the overall appearance of 'WALSANBARB' showing the colors of its foliage and flowers as true as it is reasonably possible to obtain in colored reproductions of this type. Both photographs were taken in May 2013 from one-year old plants which have been grown outdoors in 3-liter containers in the inventor's nursery in Arundel, West Sussex, United Kingdom.

BOTANICAL DESCRIPTION OF THE PLANT

Figure 1:
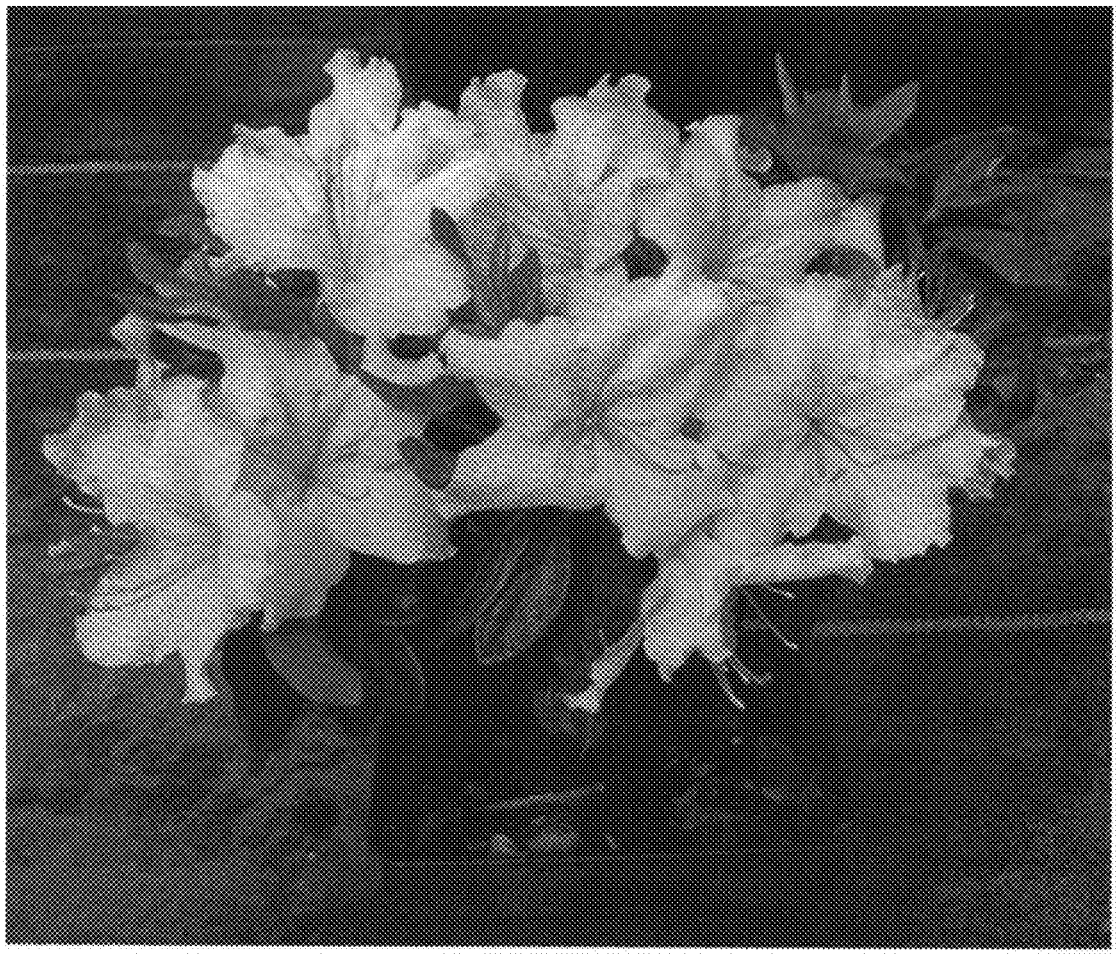
FIG. 1 depicts a whole plant of 'WALSANBARB'.
Figure 2:
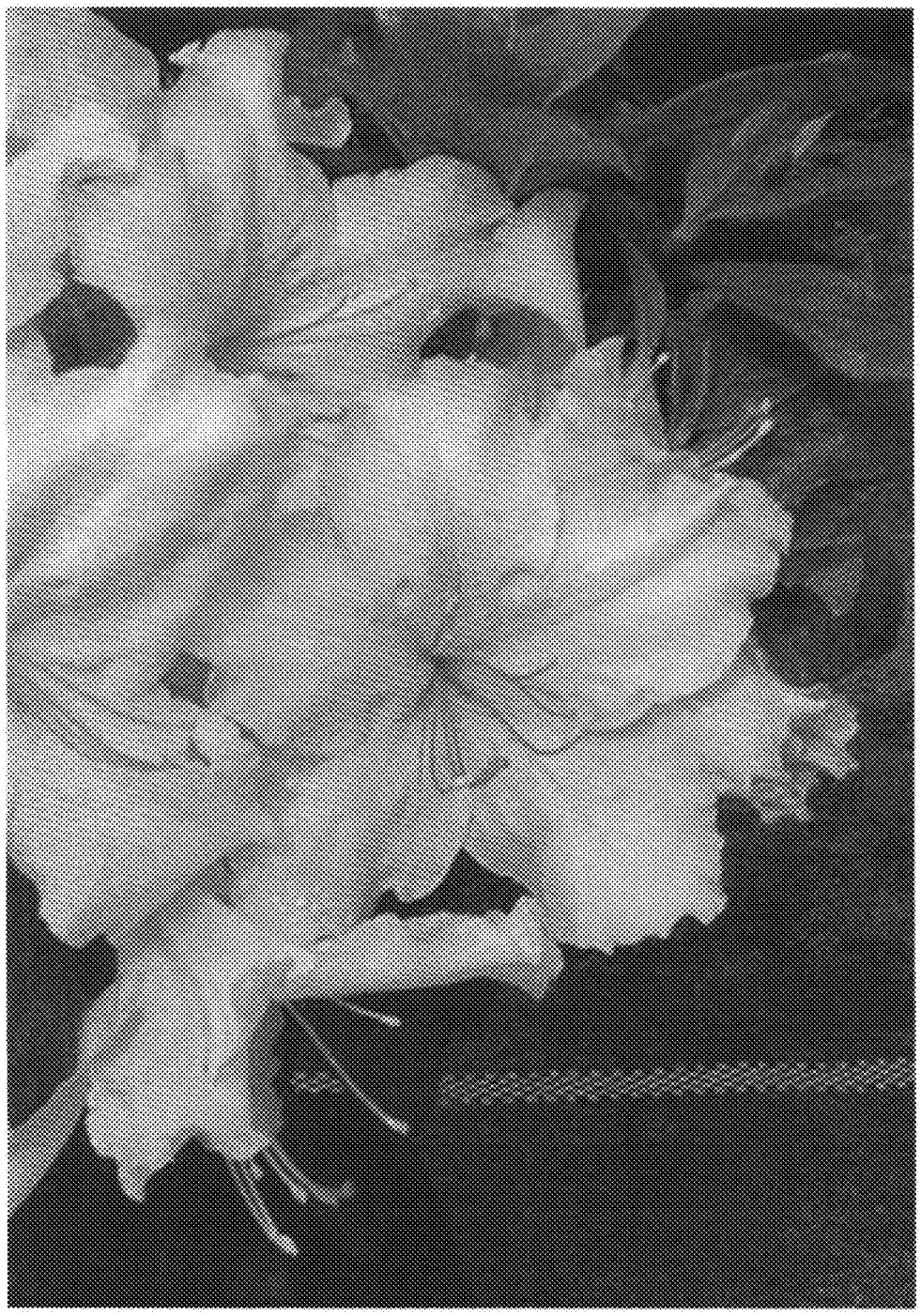
FIG. 2 depicts a close-up view of the flower of 'WALSANBARB'.

The following is a detailed description of 'WALSANBARB'. The observed plant was 2 years old and was growing out of doors in a 1 gallon container in Santa Barbara, Calif. where the botanical description was made. The color determinations are in accordance with the 2007 edition of The Colour Chart of The Royal Horticultural Society, London, England, except where general color terms of ordinary dictionary significance are used. Growing conditions are similar to those of other *Rhododendron.*

Botanical classification:
- *Family*.—Ericaceae.
- *Genus*.—*Rhododendron.*
- *Species*.—*kaempferi* hybrid.
- *Cultivar*.—'WALSANBARB'.

Parentage: Un-named seedlings raised during the breeding program; parents not retained or described.

Plant:
- *Commercial classification*.—Perennial.
- *Common name*.—Evergreen azalea.
- *Use*.—Ornamental for container or landscape.
- *Cultural requirements*.—Plant in partial shade and any free-draining slightly acidic soil.
- *Particular pest resistance or susceptibility*.—None observed.
- *Propagation method*.—Semi-ripe cuttings without use of rooting hormone.
- *Rooting system*.—Fine and fibrous.
- *Vigor*.—Moderately vigorous; lateral branching is encouraged by pinching.
- *Habit*.—Low mound.
- *Dimensions after two years*.—25 cm to 30 cm in height and 25 cm to 30 cm in width.
- *Dimensions after five years*.—30 cm to 40 cm in height and 30 cm to 40 cm in width.
- *Hardiness*.—USDA Zone 7.

Stem:
- *Dimensions*.—Length is 1.5 cm (height of manual pinch); diameter at base: 8 mm.
- *Shape*.—Cylindrical.
- *Bark*.—Texture is rough, color is 172A.
- *Number of branches*.—8.

Branches (current season extension growth):
- *Shape*.—Cylindrical.
- *Surface*.—Sparsely pubescent.
- *Dimensions*.—Length: 15 cm to 18 cm, diameter is 3 mm.
- *Color*.—144B.
- *Internode length* (*range*).—1.0 cm to 1.5 cm.

Branches (previous year's growth):
- *Shape*.—Cylindrical.
- *Dimensions*.—Length: 10 cm to 15 cm, diameter is 4 mm.
- *Color*.—172A.
- *Bark surface texture*.—Rough.
- *Internode length* (*range*).—1.0 cm to 1.5 cm.

Foliage:
- *Type*.—Evergreen.
- *Leaf arrangement*.—Alternate.
- *Leaf division*.—Simple.
- *Leaf dimensions* (*average, fully developed*).—6 cm to 7 cm in length and 3 cm in width.
- *Leaf color* (*current season new growth, adaxial surface*).—141B.
- *Leaf color* (*current season new growth, abaxial surface*).—143C.
- *Leaf color* (*mature, previous year's growth, adaxial surface*).—N137A.
- *Leaf color* (*mature, previous year's growth, abaxial surface*).—143B.
- *Leaf shape*.—Elliptic, base cuneate, apex obtuse.
- *Leaf margin*.—Ciliate, hairs very fine, silver-gray 156D.
- *Leaf surface* (*both surfaces*).—Smooth, glossy.
- *Venation*.—Pinnate, color 141B.
- *Petioles*.—Dimensions: 7 mm in length, 1.5 mm in width. Color: 145A.

Inflorescence:
- *Inflorescence type*.—Terminal.
- *Flower arrangement*.—Flowers in pairs or groups of 4 to 8.
- *Flower aspect*.—Outward.
- *Form*.—Rotate.
- *Inflorescence quantity*.—Ranges between 3 and 5 per branch and between 10 and 30 at peak of flowering.
- *Dimensions of inflorescence* (*average*).—10 cm in diameter, 8 cm in depth.
- *Blooming season*.—Late spring through early summer.
- *Lastingness of flowers* (*on the plant*).—5 to 7 days.

Bud:
- *Arrangement*.—Borne in pairs or clusters of 4 to 8 buds; initially, each bud is sheathed by a pair of modified leaf bracts which fall away as the bud swells.
- *Bud shape*.—Ovoid.
- *Dimensions* (*immediately prior to opening*).—12 mm in length and 8 mm in diameter.
- *Bracts* (*bud sheath*).—Pair, each 12 mm in length, 6 mm in width.
- *Bracts* (*bud sheath*).—Shape cupped, texture paper-like, base truncate, apex acute.
- *Bract color* (*both surfaces*).—167B.
- *Bud color* (*as bracts fall away, as bud opens*).—55C.
- *Sepals*.—5 in number, fused at base.
- *Sepal color* (*both surfaces*).—144A, surface pubescent, hairs fine, 1 to 2 mm, silver-gray 156D.
- *Sepal dimensions*.—Length: 12 mm; width: 6 mm.
- *Sepal shape*.—Ovate, base rounded, apex cuspidate.

*Sepal surface*.—Pubescent, many fine hairs 1 to 2 mm, silver-gray 156D.

*Pedicel*.—Length 12 mm, width 2 mm.

*Pedicel surface*.—Pubescent, many fine hairs 1 to 2 mm, color 144B.

Flowers:

*Form*.—Single.

*Flower dimensions*.—9 cm in diameter, 2.5 cm in depth.

*Petals arrangement*.—5 petals, overlapping, fused at base.

*Petal shape*.—Widely ovate, base truncate, apex rounded.

*Petal dimensions*.—50 mm in length, 30 mm in width.

*Petal margin*.—Smooth, gently ruffled.

*Petals*.—Color (both surfaces): Predominately 62A but ranging between 62D and 63B. Surface: Smooth, glossy.

*Venation*.—Parallel, color 63B.

*Peduncle*.—Dimensions: 5 mm in length, 2 mm in width, ribbed. Surface: Smooth. Color: 144D.

Reproductive organs:

*Stamens*.—7, length: 40 mm to 45 mm, diameter 0.5 mm, color 58C.

*Anthers*.—Shape Bifid, length 4 mm, width 1.5 mm, color 167D.

*Pollen*.—Amount is slight, color 158D.

*Pistil length*.—45 mm, diameter 0.5 mm, color 58C.

*Stigma*.—Color 158A.

*Ovary*.—Ovate, 3 mm in length, 3 mm in diameter and surrounded by dense very fine silver-gray hairs, length 5 mm, color nearest 156D.

Seed set: None observed.

COMPARISON WITH COMMERCIAL VARIETY

'WALSANBARB' may be compared with Azalea 'Blaauw's Pink' (unpatented) which also exhibits open-faced single pink flowers. 'Blaauw's Pink' is a mid-season Kurume hybrid and flowers approximately two weeks later than 'WALSANBARB' which blooms in early spring. However, the principal distinguishing characteristic of 'WALSANBARB' is its large flowers which attain a diameter of 9 cm, whereas the flowers of 'Blaauw's Pink' are typically 3.175 cm to 4.0 cm in diameter.

I claim:

1. A new and distinct variety of *Rhododendron* plant named 'WALSANBARB' as described and illustrated herein.

* * * * *